(12) United States Patent
Woo et al.

(10) Patent No.: US 8,343,397 B2
(45) Date of Patent: Jan. 1, 2013

(54) METHOD OF FORMING AN IN-EAR DEVICE

(75) Inventors: Edwin Woo, Chula Vista, CA (US);
John A. Jenkins, Jr., San Diego, CA (US)

(73) Assignee: Sperian Hearing Protection, LLC, San Diego, CA (US)

( * ) Notice: Subject to any disclaimer, the term of this patent is extended or adjusted under 35 U.S.C. 154(b) by 1620 days.

(21) Appl. No.: 11/371,651

(22) Filed: Mar. 9, 2006

(65) Prior Publication Data
US 2006/0213524 A1  Sep. 28, 2006

Related U.S. Application Data

(60) Provisional application No. 60/665,530, filed on Mar. 25, 2005.

(51) Int. Cl.
*B29C 39/18* (2006.01)
(52) U.S. Cl. .................... 264/46.4; 264/275
(58) Field of Classification Search .......... None
See application file for complete search history.

(56) References Cited

U.S. PATENT DOCUMENTS

| | | | | |
|---|---|---|---|---|
| 3,131,241 A * | 4/1964 | Mendelson | ........ | 264/257 |
| 5,044,463 A * | 9/1991 | Carr | ........ | 181/135 |
| 5,988,313 A * | 11/1999 | Håkansson | ........ | 181/135 |
| 6,264,870 B1 * | 7/2001 | Håkansson | ........ | 264/255 |
| 7,192,544 B2 * | 3/2007 | Jenkins et al. | ........ | 264/46.4 |
| 2005/0094835 A1 * | 5/2005 | Doty | ........ | 381/328 |

* cited by examiner

*Primary Examiner* — Edmund H. Lee
(74) *Attorney, Agent, or Firm* — Conley Rose, P.C.; Kristin Jordan Harkins

(57) ABSTRACT

A method for forming a device (10) that fits into a person's ear canal, that carries sound from a pipe (B) of a speaker assembly (A) into the person's ear canal, and that blocks environmental noise. A first elastomeric material (14) is molded around an elongated core (16) to form a device body (12) with an outer surface that can seal to a person's ear canal. In one method, the first elastomeric material of the body is a soft foamable material and the core is a previously-formed tube (16) of a stiffer second elastomeric material, with the body bonded to the tube by being molded around it, either in a mold cavity or by extrusion through an extrusion head. In another method, the elastomeric material of the body is a non-foam, and the core (96) is a rigid pin that is removed from the earplug body after the earplug body has at least partially solidified.

9 Claims, 3 Drawing Sheets

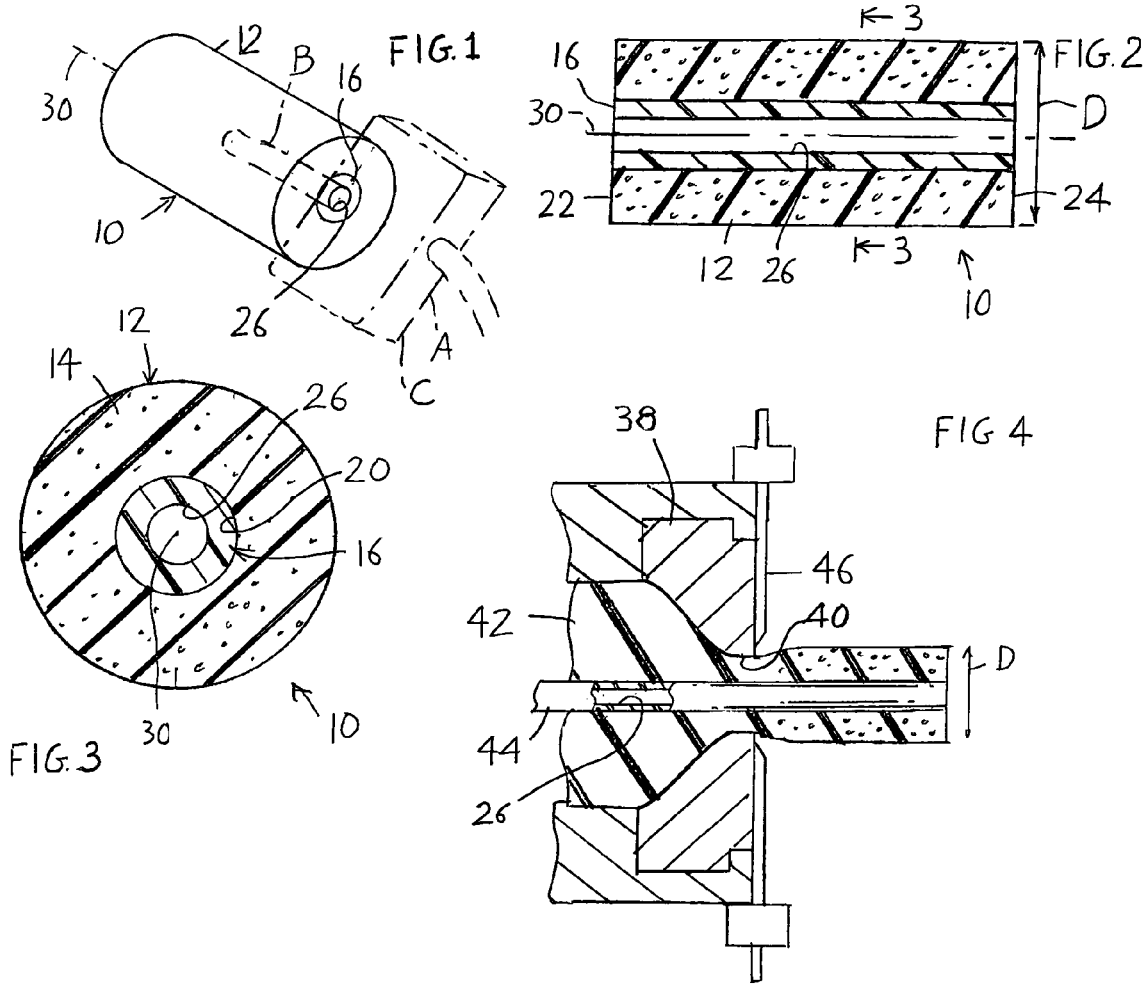

METHOD OF FORMING AN IN-EAR DEVICE

CROSS-REFERENCE

Applicant claims priority from U.S. Provisional patent application Ser. No. 60/665,530 filed Mar. 25, 2005.

BACKGROUND OF THE INVENTION

There are situations in which environmental sound is to be blocked from a person's ear while controlled sound is delivered to the ear. One situation is a communication system for use in a noisy environment, and another is a hearing test. Instead of using ear cups or earmuffs with speakers in them, a speaker can be coupled to a through hole in a simple and low cost earplug. Such earplug can be of the type worn by workers in noisy environments such as factories, but with a passage to carry sound.

One way to construct such an earplug with a passage in it, or in-ear device, is by modifying a foam elastomeric earplug of the type that is worn by workers in noisy environments such as factories to block sound. In such modification of an existing earplug, a hole is punched through the earplug to leave a passage that extends along the length of the earplug. A tube is inserted into the passage and is held in place as by adhesive. The punching of a passage in an elastomeric earplug can leave a somewhat irregular passage extending through the earplug. Adhesive applied to the tube tends to wipe off as the tube is inserted into the earplug passage, leaving an even more irregular in-ear device and with the bonding being uncertain.

SUMMARY OF THE INVENTION

In accordance with the present invention, an in-ear device and manufacturing method therefor are provided wherein the device can carry sound to a person's ear canal and block sound from other sources, wherein the device is of more regular shape and appearance and more reliable construction than previous devices of this kind, and wherein the device can be mass manufactured at low cost. One in-ear device is made by molding a first foam elastomeric material around an elongated core that is in the form of a tube. This results in a body of the first material that lies around the tube and that has a body outside surface that seals to a person's ear canal. The tube extends through substantially the entire length of the body. The body is bonded to the outside of the tube, and both are of uniform shape. In one method the body is molded in a closed cavity with the tube mounted to lie at the center of the cavity. In another method the tube is moved through the center of an opening in an extrusion head and the body is molded around the tube by flowable body material through the extrusion opening around the tube.

Another in-ear device is made by molding a nonfoam elastomeric material in a mold cavity that forms at least one flange at the outside of the body. The core is formed by a rigid pin. The core is removed to leave a through hole along the axis of the body.

The novel features of the invention are set forth with particularity in the appended claims. The invention will be best understood from the following description when read in conjunction with the accompanying drawings.

BRIEF DESCRIPTION OF THE DRAWINGS

FIG. 1 is an isometric view of an in-ear device of the present invention, with a speaker shown in phantom lines mounted on the in-ear device.

FIG. 2 is a sectional view taken along the axis of the in-ear device of FIG. 1.

FIG. 3 is a sectional view taken on line 3-3 of the earplug of FIG. 1.

FIG. 4 is a sectional view of an extrusion molding apparatus showing one method for constructing the in-ear device of FIG. 2.

DESCRIPTION OF THE PREFERRED EMBODIMENTS

Figure 5:
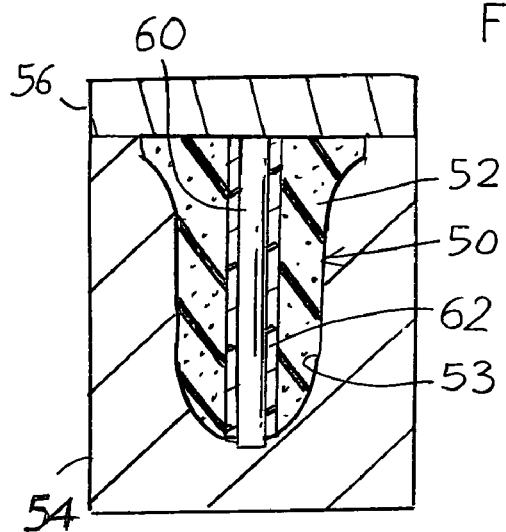
FIG. 5 is a sectional view of a cavity molding apparatus showing another method for constructing an in-ear device.

FIGS. 1-3 show an in-ear device 10 of the invention, which includes a body 12 of soft foam elastomeric polymer material 14 (an elastomeric material has a Young's Modulus of Elasticity of no more than 50,000 psi) and a tube 16 of stiffer elastomeric polymer material. The foam body has an outside diameter D of about 11 to 12 millimeters and is very soft, to seal to the walls of the person's ear canal. The tube 16 lies in a through body passage 20 of the body. The tube has an unobstructed (to sound) through tube passage 26 that extends along the length of the body between its front and rear ends 22, 24. The tube extends approximately parallel (within 100) to the earplug axis 30, and lies on the axis. Preferably the axes of the tube and body are coincident. The tube 16 is of material that is at least twice as stiff as the material of the body, which helps insertion of the device into an ear canal. In one example, the body material 14 is a resilient foam which has a Shore A number of about 2 and the tube 16 is a non-foam material which has a Shore A number of more than 12, such as about 30.

The in-ear device is used to hold a speaker, or speaker assembly A which has a narrow speaker pipe B. The speaker pipe B is rigid and lies in an interference fit in the tube passage 26 by slight expansion of the tube. It is common for a technician to pull out the earplug from a person's ear canal, by pulling on the outer case C of the speaker assembly. It is highly desirable that the speaker pipe B pull out the in-ear device when the speaker is pulled out. This requires tube walls that are resilient, but with high gripping ability. A tube material resilience level of between about 10 and 50 Shore A, together with a high interference fit (e.g. 0.5 mm) of the tube in the body of the earplug, is desirable.

Applicant provides a superior in-ear device by forming, or molding the earplug body with a through passage, by using a cavity mold or by using an extrusion mold. The material of the body is solidified around the tube during molding, to produce adhesion without using a separate adhesive, by the body material lying against the tube as the body material solidifies.

FIG. 4 shows a molding or extrusion die or head 38 with a molding opening 40 through which a foaming elastomeric polymer 42 is extruded. The opening 40 determines much of the shape of the material and therefore molds it. A continuous non-foam tube 44 (previously formed by extrusion) is a core that is fed through the extrusion head opening, so the polymer 42 is extruded around the tube. A cutting device 46 cuts the extrusion, including the polymer and tube, at intervals such as every 20 to 25 millimeters, to produce in-ear sound devices. Walls of the tube 44 extend 360° around the axis of the tube. The tube is devoid of openings in the tube sides that would allow the first material 42 of the body from flowing into the tube passage 26.

FIG. 5 shows another method for molding an in-ear device 50. The method involves pouring a solidifiable foamable polymer 52 that will form the body, into a closed cavity 53 formed in part by a lower mold part 54. A mold cover 56 includes a mold rod 60 or pin that holds a tube 62 of elastomeric material, and that forms a molding core. The mold rod 60 extends completely through the tube to block the entrance of earplug body material. The mold cover with the tube 62 temporarily mounted on the mold rod, is placed in the mold immediately after the body material is poured into the cavity or before material is injected. When the body material solidifies, the earplug is removed from the mold, and the mold rod pulled out of the tube. The body 64 adheres to the tube 62 by the fact that the body material solidified against the tube and the materials of the body and tube are bondable to each other.

The cavity molding method of FIG. 5 produces an in-ear device with a body of a desired shape and of high quality (symmetric about the axis and without irregularities), although it can cost more than the extrusion molding method of FIG. 4. Both the cavity molding and extrusion methods produce in-ear devices where the tube that extends through the body, can extend closely along the axis of the body, and the tube and body are bonded together by the body material solidifying around the tube to produce a reliable bond. The in-ear devices of the invention avoid problems of prior art in-ear devices, of poorly punched-out passages, and of poor bonding of the body to the tube and/or with adhesive material used in bonding being left at an end of the device. The presence of the tube 16, 62 of elastomeric material stiffer than the soft foam of the body 12, or at 52, has the advantage of providing a tight interference fit with the receiver pipe B, in addition to providing stiffness to enable insertion of the in-ear device into a person's ear canal (if the speaker pipe is not already in the tube).

Figure 6:
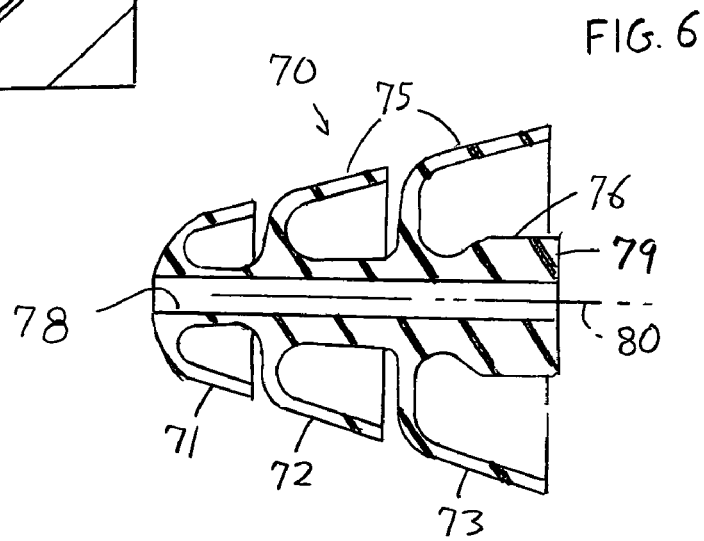
FIG. 6 is a sectional view of an in-ear device of another embodiment of the invention.
Figure 7:
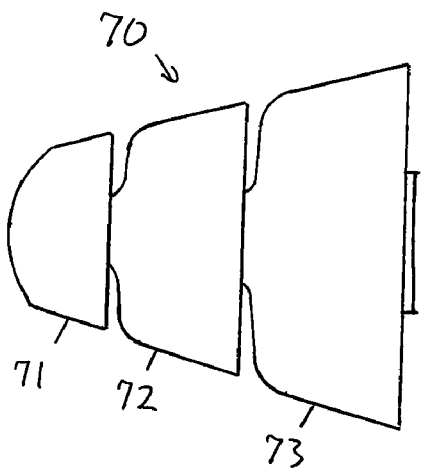
FIG. 7 is a side elevation view of the in-ear device of FIG. 6.

FIGS. 6 and 7 illustrate another in-ear device 70 of a type that is formed of non-foam elastomeric material 79. The in-ear device 70 has moderate stiffness with a Shore A number such as 15 to 35 Shore A, and has at least one thin flange (thickness preferably no more than 1 mm) 75 that provides resilience to seal to the walls of a person's ear canal. The particular in-ear device has three flanges 71-73 for sealing well to ear canals of a range of diameters, with the three flanges being supported on a stem 76. The entire in-ear device is a single molded part with a through passage 78 that extends along an axis 80 of the device.

Figure 8:
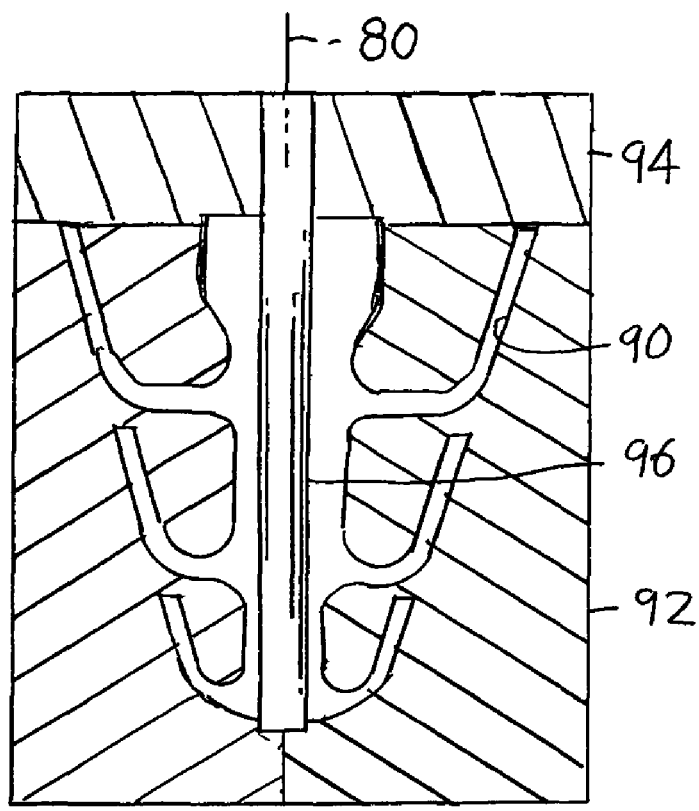
FIG. 8 is a sectional view showing a molding process for forming the through passage of the in-ear device of FIG. 6.

FIG. 8 shows that the in-ear device 70 of FIG. 6 is molded in a three-dimensional closed cavity 90 of a mold 92. One mold part 94 of the mold holds a core 96 that extends along the axis 80 of the cavity. With the core in the cavity, flowable (such as hot) elastomeric material is poured or injected into the cavity and allowed to at least partially solidify. The mold is opened and the in-ear device is removed from the cavity, and the core pulled out of the device passage. The moderate stiffness elastomeric material of the in-ear device 70 enables the walls of its passage 78 to tightly grip the pipe of the speaker.

Figure 9:
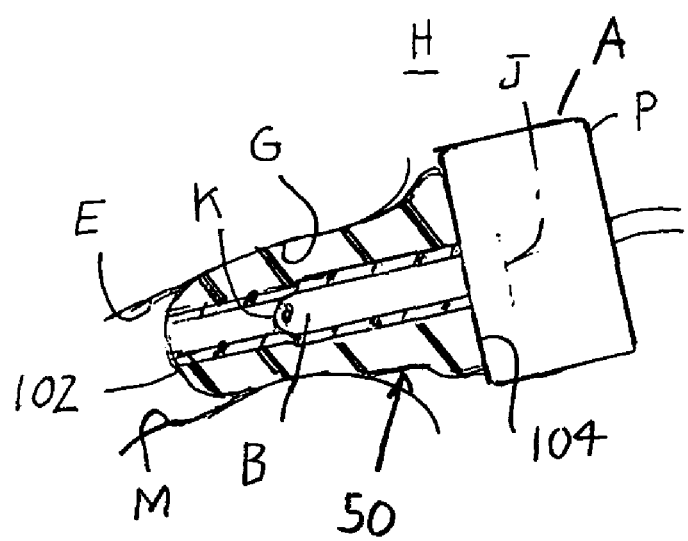
FIG. 9 is a sectional view showing the in-ear device of FIG. 5 inserted into a person's ear canal and with the speaker of FIG. 1 installed in the device.

FIG. 9 shows an in-ear device 50 lying in the outer portion G of a person's ear canal E, to block sound from the environment H from entering the inner portion M of the ear canal. The device has an inner end 102 lying in the ear canal and an outer end 104 lying outside the ear canal. The speaker assembly A includes a vibrating sound generating element J that lies in a housing P and generates sound that passes through the pipe B and out of an open end K of the pipe into the inner portion M of the ear canal.

Thus, the invention provides an in-ear device of quality appearance and ruggedness, which can be manufactured at low cost. The in-ear device also has a through passage with resilient walls that are stiff enough to provide a tight interference fit with a speaker pipe and allow the pipe to be installed by pushing it by hand into the passage. The in-ear device is made by molding an elastomeric material around an elongated core. Such molding can be accomplished for an in-ear device that includes a soft elastomeric foam body and a stiffer elastomeric tube extending along the axis of the body, by molding in a closed cavity or by molding in the course of extrusion. An in-ear device that comprises a body of non-foam elastomeric material with a flange, can be made by placing flowable elastomeric material in a closed cavity that includes a core that extends through the cavity. The core is removed from the body after the body has solidified at least partially.

Although particular embodiments of the invention have been described and illustrated herein, it is recognized that modifications and variations may readily occur to those skilled in the art, and consequently, it is intended that the claims be interpreted to cover such modifications and equivalents.

What is claimed is:

1. A method for forming an in-ear device that carries sound from a speaker into a person's ear canal while preventing almost all environmental sound from reaching the person's ear canal inner portion, comprising:
    molding a foam elastomeric material around an elongated tube that has a tube axis and a tube passage extending along said axis, to form a device body with a body axis that is parallel and coincident to the tube axis, with a body outer surface of a shape to fit into and seal against an outer portion of a persons ear canal, and with said tube passage extending along said axis;
    said step of molding including molding the entire length of the body around said tube;
    said step of molding includes fixing the position of said tube in a closed cavity by at least one pin that has portions that fill at least opposite ends of the tube passage, filling the cavity with said foam elastomeric material and allowing the foam to solidify against the body to adhere thereto, and removing from the cavity the earplug body with the tube therein, including removing the at least one pin from the tube passage.

2. The method of claim 1, wherein the elongated tube is elastomeric.

3. The method of claim 1, Wherein the device body lies around said tube.

4. The method of claim 2, wherein the foam elastomeric material of the device body bonds to the elastomeric material of the tube when the foam solidifies.

5. The method of claim 1, wherein adhesive is not applied to hold the tube to the device body.

6. The method of claim 4, wherein the foam elastomeric material of the device body bonds to the elastomeric material of the tube without adhesive.

7. The method of claim 1, wherein:
    the elongated tube comprises elastomeric material;
    the device body lies around the tube; and
    the foam elastomerie material of the device body bonds to the elastomeric material of the tube when the foam solidifies.

8. The method of claim 7, wherein adhesive is not applied to hold the tube to the device body.

9. The method of claim 7, wherein the foam elastomeric material of the device body bonds to the elastomeric material of the tube without adhesive.

* * * * *